United States Patent [19]

Ito et al.

[11] Patent Number: 4,876,371

[45] Date of Patent: Oct. 24, 1989

[54] PROCESS OF PRODUCING GLYCIDYL ETHERS OF MONOHYDRIC OR POLYHYDRIC PHENOLS

[75] Inventors: Iko Ito; Yoshiki Toyoshima, both of Ehime; Hisao Takagishi, Kyoto; Tsutomu Takahashi, Ehime, all of Japan

[73] Assignee: Sumitomo Chemical Company, Limited, Osaka, Japan

[21] Appl. No.: 56,319

[22] Filed: May 29, 1987

Related U.S. Application Data

[63] Continuation of Ser. No. 650,465, Sep. 14, 1984, abandoned, which is a continuation-in-part of Ser. No. 489,296, Apr. 28, 1983, abandoned.

[30] Foreign Application Priority Data

Apr. 28, 1982 [JP] Japan ................................ 57-71838
Apr. 28, 1982 [JP] Japan ................................ 57-71839

[51] Int. Cl.$^4$ .......................................... C07D 301/28
[52] U.S. Cl. ............................................. 549/517
[58] Field of Search ................................... 549/517

[56] References Cited

U.S. PATENT DOCUMENTS

| | | | |
|---|---|---|---|
| 3,033,817 | 5/1962 | Price et al. | 549/517 |
| 3,325,452 | 6/1967 | McWhorter et al. | 549/517 |
| 3,372,142 | 3/1968 | Smith | 549/517 |
| 3,417,050 | 12/1968 | Price et al. | 549/517 |
| 4,072,656 | 2/1978 | Hartmann | 549/517 |
| 4,130,549 | 12/1978 | Ueno et al. | 549/517 |
| 4,132,718 | 1/1979 | Vargiu et al. | 549/517 |
| 4,373,073 | 2/1983 | Wojtech et al. | 549/517 |

FOREIGN PATENT DOCUMENTS 1050641 12/1966 United Kingdom .
1493538 11/1977 United Kingdom .

OTHER PUBLICATIONS

Abstract of Japan 63974 (May 1981).
Chemical Abstracts 94:209461m (1981).
Chemical Abstracts 54: 1543b (1960).
Yoshio Tanaka et al, J. Macromol. Sci.-Chem. A1(8), Dec. 1967, pp. 1469-1485.

*Primary Examiner*—Richard L. Raymond
*Assistant Examiner*—Ba Trinh
*Attorney, Agent, or Firm*—Sughrue, Mion, Zinn, Macpeak and Seas

[57] ABSTRACT

A process of producing glycidyl ethers of monohydric or polyhydric phenols is disclosed, which comprises mixing a monohydric or polyhydric phenol, dioxane or diethoxyethane, and epichlorohydrin; adding to the mixture an aqueous solution of an alkali metal hydroxide and subjecting to azeotropic distillation water, dioxane or diethoxyethane, and epichlorohydrin, followed by liquefaction of the distillate to be divided into an aqueous layer and an organic layer, and circulating the organic layer to the mixture whereas eliminating the aqueous layer. According to this process, the content of hydrolyzable chlorine which cannot be removed in a subsequent purification step is minimized and the phenol glycidyl ethers thus obtained are well suited for the use of sealing materials for integrated circuits.

1 Claim, No Drawings

PROCESS OF PRODUCING GLYCIDYL ETHERS OF MONOHYDRIC OR POLYHYDRIC PHENOLS

CROSS REFERENCE OF RELATED APPLICATION

This is a continuation Ser. No. 650,465 filed Sept. 14, 1984 now abandoned which is a continuation in part of application Ser. No. 489,296 filed Apr. 28, 1983, now abandoned.

FIELD OF THE INVENTION

The present invention relates to a process of producing epoxy resins, so called glycidyl ethers of phenols, mainly utilized for the electric and electronic industries.

BACKGROUND OF THE INVENTION

It is mandatorily required for glycidyl ethers of phenols utilized for electric and electronic materials that the content of hydrolyzable chlorine be small, and such has been widely recognized in the art. That is, hydrolyzable chlorine results in adverse effects such as deterioration of electrical insulation, corrosion of lead wires, etc. Particularly with glycidyl ethers of phenols as encapsulation materials for integrated circuits using semiconductors, it is essential that the content of hydrolyzable chlorine be small. For example, in integrated circuits having an integration density of 64 killobits or more, it is required that the content of hydrolyzable chlorine be not greater than 600 ppm.

To reduce hydrolyzable chlorine, various processes for production have been studied. For example, a process of producing glycidyl ether of bisphenol A which comprises gradually feeding an aqueous solution of sodium hydroxide to a solution of bisphenol A in epichlorohydrin, wherein water is distilled off azeotropically with epichlorohydrin at low temperatures under reduced pressure and the distilled-off epichlorohydrin is circulated into the reaction system, is described in Japanese Patent Publication No. 36000/78. In the examples of the above patent publication, the content of hydrolyzable chlorine is shown to be 1200 to 4500 ppm and no sufficient improvement effect is obtained thereby. In Japanese Patent Application (OPI) Nos. 90400/79 (the term "OPI" used herein refers to an unexamined but published patent application) and in Japanese Patent Application (OPI) No. 13596/79 and U.S. Pat. No. 3,121,727, processes of producing glycidyl ethers of polyhydric phenols characterized by adding an alcohol to a solution of polyhydric phenols in epihalohydrins are described. With respect to the examples of these patent publications or patent the content of hydrolyzable chlorine in glycidyl ether of bisphenol A obtained from bisphenol A and epichlorohydrin is approximately 1000 ppm and the total chlorine content is from 1500 to 3500 ppm in the case of Japanese Patent Application (OPI) No. 90400/79; and a content of hydrolyzable chlorine in glycidyl ether of phenol novolak obtained from phenol novolak and epichlorohydrin is 1500 ppm in the case of Japanese Patent Application (OPI) No. 13596/79. Such are not sufficiently improved results, however. Further, it is mentioned in the patent publications or patent as cited above that moisture may not be removed from the reaction system. However, it is well known that epichlorohydrin is decomposed even in the co-presence of water, which is disadvantageous from the industrial viewpoint. Further, there is described in Japanese Patent Publication No. 46981/77 a process for producing glycidyl ether of phenols which comprises reacting phenols with an excess of epichlorohydrin using quaternary ammonium salts or quaternary ammonium bases as addition catalysts in a first step to prepare chlorohydrin ethers of phenols, and then adding anhydrous sodium hydroxide to effect dehydrochlorination from the chlorohydrin ether group. According to the examples of this patent publication, only glycidyl ethers of phenols having a content of hydrolyzable chlorine of 1000 ppm were produced. In Japanese Patent Application (OPI) No. 141479/80, a process of producing glycidyl ethers of phenols which comprises preparing chlorohydrin ethers of phenols from phenols and epichlorohydrin using addition catalysts such as quaternary ammonium salts or the like, removing an excess of epichlorohydrin by distillation, and then effecting dehydrochlorination using an aqueous solution of alkali metal hydroxides is described. In the examples thereof, the content of hydrolyzable chlorine in the glycidyl ethers of phenols is 700 ppm or more, and no sufficient improvement effect is obtained thereby.

It is known that in epoxidation in which glycidyl ethers of phenols are produced from phenols and epichlorohydrin, the reaction takes place in two steps. When taking phenol as an example, glycidyl ether of phenol is produced in two steps of addition reaction and cyclization reaction as described below:

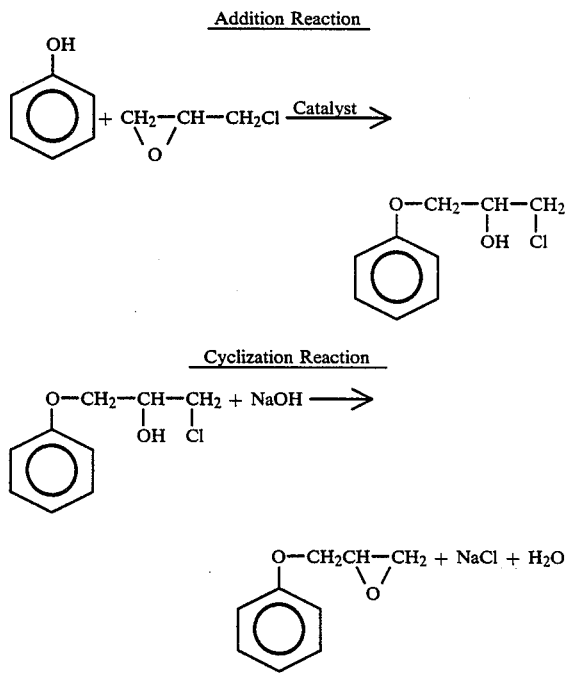

The intermediate, 1,2-chlorohydrin ether of phenol, in part induces hydrolyzable chlorine, but this 1,2-chlorohydrin ether of phenol is easily cyclized in a subsequent purification step as defined below to convert into glycidyl ether of phenol. The term "purification step" as used herein refers to a reaction step in which the 1,2-chlorohydrin ether group is converted into the glycidyl ether group through cyclization reaction by adding sodium hydroxide to an aromatic hydrocarbon solution or ketone solution of glycidyl ethers of phenols containing a small quantity of 1,2-chlorohydrin ether of phenols obtained in the epoxidation.

The hydrolyzable chlorine which comes into question in the present invention cannot be removed by the aforesaid purification step and has the following structure in the case of phenol:

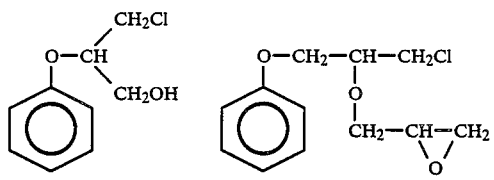

These hydrolyzable chlorines are impurities produced by side reactions in the epoxidation and cannot be removed by the purification step described above.

As a result of extensive investigations on attempting to obtain glycidyl ethers of phenols containing as little hydrolyzable chlorine as possible, the present inventors have reached the present invention.

SUMMARY OF THE INVENTION

The present invention relates to a process of producing glycidyl ethers of monohydric or polyhydric phenols which comprises:

mixing a monohydric or polyhydric phenol, dioxane or diethoxyethane, and epichlorohydrin, adding to the mixture an aqueous solution of an alkali metal hydroxide and subjecting to azeotropic distillation water, dioxane or diethoxyethane, and epichlorohydrin, followed by liquefaction of the distillate to be divided into an aqueous layer and an organic layer, and circulating the organic layer to the mixture whereas eliminating the aqueous layer.

According to the present invention, it became possible to produce monohydric or polyhydric phenol glycidyl ethers having a minimized content of hydrolyzable chlorine.

DETAILED DESCRIPTION OF THE INVENTION

An advantage of the present invention lies in preventing side reactions in which hydrolyzable chlorine incapable of being removed in a subsequent purification step is likely to be produced, in a step of epoxidation.

A first feature of the present invention is that dioxane or diethoxyethane is present in the epoxidation reaction so that side reactions producing hydrolyzable chlorine incapable of being removed in a purification step can be prevented.

A second feature of the present invention is that in addition to dioxane or diethoxyethane, catalytically acceptable amounts of quaternary ammonium salts or quaternary ammmonium bases are further present in the epoxydation reaction. In this regard, the advantage of the present invention is described in detail below.

The alkali metal hydroxides act both as catalysts of the aforesaid addition reaction in the epoxidation and as reactants in the cyclization reaction. In the citations as described above, the processes are characterized by performing addition reaction using quaternary ammonium salts or quaternary ammonium bases as addition catalysts. Further, these processes are also characterized by the absence of any alkali metal hydroxide in the addition step. In this case, it is assumed that solutions of the reaction system are neutral to acidic. On the other hand, quaternary ammonium salts or quaternary ammonium bases used in the present invention have a characteristic of acting as phase transfer catalysts in the presence of alkali metal hydroxides. In this regard, these compounds are used for purposes dissimilar to those in the citations as described above. Further, in this case, solutions in the reaction system are alkaline. Furthermore, the present invention is advantageous in that side reactions for producing hydrolyzable chlorine incapable of being removed in the purification step can be prevented, which is not observed in the prior art processes.

Illustrative examples of the monohydric or polyhydric phenols which can be used in the present invention include monohydric or polyhydric phenols comprising a phenol unit unsubstituted or substituted with a halogen atom, an alkyl group, an allyl group, an alkenyl group, an aryl group or an aralkyl group. Specific examples include phenol, o-cresol, m-cresol, p-cresol, diphenolmethane (bisphenol F), diphenolethane, diphenolpropane (bisphenol A), tetrabrominated bisphenol A, 1,1-bis(4-hydroxyphenyl)-1-phenylethane, 1,1-bis(4-hydroxyphenyl)-1,1-dimethylmethane, phenol novolak, brominated phenol novolak, o-cresol novolak, resorcin novolak, brominated resorcin novolak, resorcin, hydroquinone, methylresorcinol, tetrachlorinated bisphenol A, etc. But the present invention is not limited thereto.

Illustrative examples of the alkali metal hydroxides which can be used in the present invention include sodium hydroxide, potassium hydroxide and the like. The alkali metal hydroxide is used in an amount of 0.9 to 1.1 mols per mol of the phenolic hydroxy group. In case that the amount of the alkali metal hydroxide used is less than 0.9 mol, the amount of gels formed as by-products is small and such is advantageous; however, hydrolyzable chlorine to be removed in the aforesaid purification step remains unremoved. In case that the amount of the alkali metal hydroxide is less than 0.9 mol, the cyclization is not completed so that hydrolyzable chlorine to be removed in the purification step remains unremoved as a natural consequence. In this case, an additional purification step is required and such is disadvantageous from the industrial viewpoint. On the other hand, in case that the amount of the alkali metal hydroxide is more than 1.1 mols, the amount of gels formed as by products increases and such is disadvantageous in the production of desired product.

It is preferred that the amount of epichlorohydrin used in the present invention is in the range of from 2.5 to 20 mols, more preferably in the range of from 4 to 10 mols, per mol of the phenolic hydroxy group. This is because a lesser amount of epichlorohydrin results in disadvantages from the industrial viewpoint such as deterioration in product quality, e.g., increase in melt viscosity of glycidyl ethers of phenols due to the formation of high molecular weight substances by intermolecular reactions and further increase of gel formation, etc. On the other hand, a larger amount of epichlorohydrin also results in disadvantages from the industrial viewpoint such as increase of the volume of the reaction mixture leading to reduction in productivity.

It is preferred that the amount of dioxane or diethoxyethane is in the range of from 10 to 100 parts by weight per 100 parts by weight of epichlorohydrin. With the amount of less than 10 parts by weight, the effect contemplated in the present invention is not remarkable. When the amount exceeds 100 parts by weight, industrial disadvantages such as reduction in productivity due to increase of the volume of the reaction mixture, etc. are involved.

Specific examples of the quaternary ammonium salts or quaternary ammonium bases which can be used in the present invention include tetramethylammonium chloride, benzyltrimethylammonium chloride, benzyltriethylammonium chloride, benzyltributylammonium chloride, tetrabutylammonium bromide, tetrabutylammonium hydrogen sulfite, trioctylmethylammonium chloride, chlorine chloride, benzyltrimethylammonium hydroxide, tetrabutylammonium hydroxide, etc. But the present invention is not limited thereto. While it is not particularly limited, it is preferred that the amount of the quaternary ammonium salts or quaternary ammonium bases be not less than 0.003 mol per mol of the phenolic hydroxy group. With an amount of less than 0.003 mol, the effect of reducing hydrolyzable chlorine is insufficient.

One embodiment of the process of the present invention is described below:

An aqueous solution of an alkali metal hydroxide is continuously added to a solution of a monohydric or polyhydric phenol in epichlorohydrin and a solution of dioxane or diethoxyethane and optionally, a quaternary ammonium salt or a quaternary ammonium base. Water, epichlorohydrin and dioxane or diethoxyethane are removed from the reaction mixture by azeotropic distillation, and the distillate is liquefied and divided into an aqueous layer and an organic layer. The organic layer is circulated to the reaction mixture, and the aqueous layer is eliminated. By controlling the water content in the reaction system to a lesser amount, decomposition of epichlorohydrin can be prevented. In this case, it is preferred that the water content in the reaction system be in the range of from 0.2 to 2.5 wt%. With the water content of less than 0.2 wt%, gels are formed during the reaction and industrial disadvantage results. With the water content of more than 2.5 wt%, the effect of preventing epichlorohydrin from decomposition is poor.

Compositions mainly composed of glycidyl ethers of monohydric or polyhydric phenols produced in the process of the present invention, additionally containing hardners such as phenol novolak, diaminodiphenylmethane, diaminodiphenylsulfone, m-phenylenediamine, phthalic anhydride, tetrahydrophthalic anhydride, pyrromellitic anhydride, benzophenone tetracarboxylic anhydride, etc.; inorganic fillers such as silica, alumina, talc, clay, glass fibers, etc.; hardening accelerators such as imidazoles, tertiary amines, phenols, etc.; internal release agents such as stearic acid, calcium stearate, carnava wax, montan wax, etc.; and if desired, flame-retardants such as glycidyl ether of tetrabromobisphenol, etc. are advantageously usable as materials suited for electric and electronic industries, particularly as encapsulating agents for integrated circuits. Of glycidyl ethers of monohydric or polyhydric phenols produced in the process of the present invention, the glycidyl ether of o-cresol novolak is particularly advantageously usable as an encapsulating agent for integrated circuits having an integration density of 64 killobit or more since the content of impurities such as hydrolyzable chlorine, etc. is particularly minimized.

The term "epoxy equivalent" as used herein is defined by the molecular weight per mole of the glycidyl ether group. Further, the term "hydrolyzable chlorine" is used to refer to the content of chlorine ions expressed by weight percent of chlorine atoms in a monohydric or polyhydric phenol glycidyl ether compound, the chlorine ions being released when an alcohol solution of potassium hydroxide is added to a solution of the monohydric or polyhydric phenol glycidyl ether compound in dioxane and the mixture is heated for 30 minutes under reflux and quantitatively determined with a silver nitrate solution by back titration.

Hereafter the present invention will be described in detail with reference to the examples but is not deemed to be limited thereto.

EXAMPLES 1 TO 7 AND COMPARISON EXAMPLES 1 AND 2

Using a 1 liter volume of a separatable flask equipped with a thermometer, a dropping funnel, a condenser and a stirrer, a phenol was dissolved in epichlorohydrin in each of the compositions as shown in Table 1. In Examples 1 to 7, an ether compound having the kind and amount as shown in Table 1 was used. After the system reached and condition of temperature and pressure as shown in Table 1, an aqueous solution of sodium hydroxide was continuously added to the system over 5 hours. During the reaction, the water, epichlorohydrin and ether compound evaporated due to azeotropy. The evaporated compounds were cooled and liquefied in the condenser. The liquid was separated into an organic layer and an aqueous layer. The organic layer was returned to the reaction system, whereas the aqueous layer was eliminated from the reaction system. Thus the water from the aqueous solution of sodium hydroxide and that generated by the reaction were eliminated from the reaction system. After completion of the addition of the aqueous solution of sodium hydroxide, the reaction was matured for 1 hour under the condition of temperature and pressure as shown in Table 1. At this time, the condition of temperature and pressure is a condition of the water, epichlorohydrin and ether compound for the azeotropy with respect to temperature and pressure.

After completion of the reaction, the unreacted epichlorohydrin, ether compound and a trace amount of water were removed by distillation under reduced pressure. The glycidyl ether of phenol, containing salts formed as by-products, obtained in this step was dissolved in methyl isobutyl ketone and the by-product salts were removed by filtration. By distillation under reduced pressure, the methyl isobutyl ketone was removed to obtain the glycidyl ether of phenol.

The content of hydrolyzable chlorine and epoxy equivalent in the thus obtained glycidyl ether of phenol are shown in Table 1.

TABLE 1

| Run No. | Kind of Phenol | Amount of Phenol (g) | Epichlorohydrin (g) | NaOH (48% aq. solution) (g) | Kind and Amount of Ether Compound (g) | Reaction Pressure/ Reaction Temperature (mmHg/°C.) | Hydrolyzable Chlorine of the Product (ppm) | Epoxy Equivalent |
|---|---|---|---|---|---|---|---|---|
| Example 1 | o-Cresol Novolak | 110 (0.917)* | 594 (6.42)** | 76.4 (0.917)*** | Dioxane 237 | 156/61 | 390 | 203 |
| Example 2 | " | " | " | " | Diethoxyethane | 150/69 | 350 | 200 |

TABLE 1-continued

| Run No. | Kind of Phenol | Amount of Phenol (g) | Epichloro-hydrin (g) | NaOH (48% aq. solution) (g) | Kind and Amount of Ether Compound (g) | Reaction Pressure/ Reaction Temperature (mmHg/°C.) | Hydrolyzable Chlorine of the Product (ppm) | Epoxy Equivalent |
|---|---|---|---|---|---|---|---|---|
| Example 3 | " | 150 (1.25) | 463 (5.01) | 104 (1.25) | Dioxane 237 | 150/56 | 520 | 213 |
| Example 4 | " | 110 (0.917) | 594 (6.42) | 76.4 (0.917) | Dioxane 277 | 250/72 | 380 | 195 |
| Example 5 | " | " | " | " | Dioxane 237 | 150/60 | 350 | 203 |
| Example 6 | " | " | " | 80.2 (0.962) | Dioxane 365 | 150/61 | 430 | 197 |
| Example 7 | Phenol Novolak | 110 (1.04) | 685 (7.41) | 88.2 (1.06) | Dioxane 237 | 150/61 | 410 | 187 |
| Comparison Example 1 | o-Cresol Novolak | 150 (1.25) | 809 (8.75) | 104 (1.25) | none | 150/65 | 650 | 198 |
| Comparison Example 2 | " | 150 (1.25) | 463 (5.01) | 104 (1.25) | none | " | 870 | 207 |

*Mol number of Phenolic OH Group
**Mol number of Epichlorohydrin
***Mol number of NaOH While Example 1 differs from Comparison Example 1 in absolute amounts of phenol, epichlorohydrin and sodium hydroxide, relative amounts (molar ratio) of these compounds are the same. Further, the reaction temperatures are somewhat different from each other but such difference is due to a difference in the presence or absence of the ether compound. Accordingly, substantially the same reaction conditions were used between Example 1 and Comparison Example 1 except that the ether compound is present or absent. The content of hydrolyzable chlorine in Example 1 wherein the ether compound was used showed 390 ppm, whereas the content was 650 ppm in Comparison Example 1 in which no ether compound was used. Thus, an effect of reducing hydrolyzable chlorine was remarkable when the ether compound was used. Further, in Example 5 in which an ether compound was employed in an amount greater than that of Example 1, the content of hydrolyzable chlorine was further reduced to 350 ppm.

EXAMPLES 8 TO 12 AND COMPARISON EXAMPLES 3 AND 4

Using the same apparatus as used in Example 1, glycidyl ethers of phenols were produced from phenols and epichlorohydrin. After the phenol, epichlorohydrin and ether compound had been homogeneously dissolved, a quaternary ammonium salt or a quaternary ammonium base was added thereto and dissolved therein. After the solution was set under a given temperature and pressure condition, an aqueous solution of an alkali metal hydroxide was continuously added to the solution over 4 hours. After completion of the reaction, the unreacted epichlorohydrin, ether compound and a trace amount of water remained were removed by distillation under reduced pressure. The glycidyl ether of phenol, containing salts formed as by-products, obtained in this state was dissolved in methyl isobutyl ketone, and warm water was further added to the solution to dissolve the by-product salts and quaternary ammonium salt or quaternary ammonium base therein. Thereafter, the organic layer and the aqueous layer were separated from each other. A part of the organic layer was taken up and the content of hydrolyzable chlorine in the glycidyl ether of phenol was measured. If desired, NaOH corresponding to 4 molar times that of hydrolyzable chlorine was added as a 10 wt% aqueous solution thereof to the methyl isobutyl ketone solution containing the glycidyl ether of phenol. The mixture was treated at 60° C. for 2 hours. Thereafter, an excess of NaOH was neutralized with sodium phosphite and the by-product salts were removed by washing with water. Finally, a trace amount of water contained in the methyl isobutyl ketone containing the glycidyl ether of phenol was removed by distillation, and the salts remained in trace amounts were removed by filtration. Then, the methyl isobutyl ketone was removed by distillation under reduced pressure to obtain the glycidyl ether of phenol.

Kinds, charged amounts and mol numbers of respective components, reaction conditions and the like in the respective examples are shown in Table 2. In Table 3, the content of hydrolyzable chlorine and epoxy equivalent in the obtained glycidyl ether of phenol are shown.

TABLE 2

| Run No. | Kind of Phenol | Amount of Phenol (g) | Epichloro-hydrin (g) | NaOH (48% aq. solution) (g) | Kind of Quaternary Ammonium Salt or Quaternary Ammonium Base | Amount of the Salt or Base (g) | Kind and Amount of Ether Compound (g) | Reaction Pressure/ Reaction Temperature (mmHg/°C.) | Purification |
|---|---|---|---|---|---|---|---|---|---|
| Example 8 | o-Cresol Novolak | 110 (0.917)* | 509 (4.59)** | 80.2 (0.96)** | tetramethyl-ammonium chloride | 2.01 (0.018)** | Dioxane 204 | 150/61 | no |
| Example 9 | " | " | " | 76.4 (0.917) | benzyltrimethyl-ammonium chloride | 1.70 (0.0092) | " | " | yes |
| Example 10 | " | " | " | " | tetrabutyl-ammonium chloride | 5.79 (0.018) | " | " | yes |
| Example 11 | " | " | " | " | benzyltrimethyl-ammonium hydroxide | 3.00 (0.018) | " | " | yes |
| Example 12 | Phenol | 110 | 685 | 88.2 | trioctylmethyl- | 12.59 | Diethoxyethane | 150/69 | yes |

TABLE 2-continued

| Run No. | Kind of Phenol | Amount of Phenol* (g) | Epichloro-hydrin (g) | NaOH (48% aq. solution) (g) | Kind of Quaternary Ammonium Salt or Quaternary Ammonium Base | Amount of the Salt or Base** (g) | Kind and Amount of Ether Compound (g) | Reaction Pressure/ Reaction Temperature (mmHg/°C.) | Purification |
|---|---|---|---|---|---|---|---|---|---|
| Comparison Example 3 | Novolak o-Cresol Novolak | (1.04) 110 (0.917) | (7.41) 509 (4.59) | (1.06) 76.4 (0.917) | ammonium chloride trioctylmethyl-ammonium chloride | (0.01) 11.10 (0.028) | 274 none | 150/65 | yes |
| Comparison Example 4 | " | " | " | " | benzyltriethyl-ammonium chloride | 6.26 (0.028) | none | " | no |

*Mol number of Phenolic OH Group
**Mol number

TABLE 3

| | Analytical Date | |
|---|---|---|
| Run No. | Epoxy Equivalent | Hydrolyzable Chloride (ppm) |
| Example 8 | 211 | 300 |
| Example 9 | 208 | 270 |
| Example 10 | 202 | 250 |
| Example 11 | 209 | 270 |
| Example 12 | 189 | 320 |
| Comparison Example 3 | 214 | 650 |
| Comparison Example 4 | 201 | 1790 |

As is evident from Table 3, the content of hydrolyzable chlorine of glycidyl ether of phenol obtained in Examples 8 through 12 showed 250 to 320 ppm, whereas that in Comparison Examples 3 and 4 was as high as 650 to 1790 ppm. Thus, difference from Examples 8 and 9 is obviously noted. Comparison Examples 1 and 2 are identical with the process generally employed in the art. By merely adding a quaternary ammonium salt, the content of hydrolyzable chlorine becomes rather high as shown in Comparison Example 4.

While the invention has been described in detail and with reference to specific embodiments thereof, it will be apparent to one skilled in the art that various changes and modifications can be made therein without departing from the spirit and scope thereof.

What is claimed is:

1. A process of producing glycidyl ethers of monohydric or polyhydric phenols which comprises:

mixing a monohydric or polyhydric phenol, dioxane or diethoxyethane, and epichlorohydrin, wherein the amount of dioxane or diethoxyethane is in the range of 10 to 100 parts by weight per 100 parts by weight of epichlorohydrin, and the amount of epichlorohydrin is in the range of 2.5 to 20 mols per mol of the phenolic hydroxy group, gradually adding to the mixture an aqueous solution of an alkali metal hydroxide in an amount in the range of 0.9 to 1.1 mols per mol of the phenolic hydroxyl group and subjecting to azeotropic distillation water, dioxane or diethoxyethane, and epichlorohydrin at a temperature of about 56° C. to about 72° C. and a pressure of about 150 mmHg to about 250 mmHg, maintaining the water content of the mixture in the range of from 0.2 to 2.5 wt%, followed by liquefication of the distillate to be divided into an aqueous layer and an organic layer, and circulating the organic layer to the mixture whereas eliminating the aqueous layer.

* * * * *